United States Patent [19]

Tripathi et al.

[11] 4,263,277

[45] Apr. 21, 1981

[54] COLD PERMANENT WAVE COMPOSITION AND METHOD CONTAINING 2-IMINOTHIOLANE

[75] Inventors: Uma P. Tripathi, Oakland, N.J.; Diana K. Tomaszewicz, Timonium, Md.

[73] Assignee: American Cyanamid Company, Stamford, Conn.

[21] Appl. No.: 50,359

[22] Filed: Jun. 20, 1979

[51] Int. Cl.³ .......................... A61K 7/09; A45D 7/00
[52] U.S. Cl. ............................................. 424/72; 132/7
[58] Field of Search ............................... 424/72; 132/7

[56] References Cited

U.S. PATENT DOCUMENTS

| | | | |
|---|---|---|---|
| 2,615,828 | 10/1952 | Haefele | 424/72 X |
| 2,631,965 | 3/1953 | Schnell | 424/72 |
| 3,223,585 | 12/1965 | Addor | 424/275 |
| 3,317,562 | 5/1967 | Addor | 424/275 |
| 3,318,910 | 5/1967 | Addor | 424/275 |
| 3,950,532 | 4/1976 | Bouillon et al. | 424/72 |

*Primary Examiner*—Dale R. Ore
*Attorney, Agent, or Firm*—Charles J. Fickey

[57] ABSTRACT

Compositions for waving hair of the cold wave type containing 2-iminothiolane.

6 Claims, No Drawings

COLD PERMANENT WAVE COMPOSITION AND METHOD CONTAINING 2-IMINOTHIOLANE

FIELD OF THE INVENTION

The present invention relates to permanent waving of human hair, to compositions for effecting a wave in hair, and to methods for utilizing them. More particularly, the invention relates to cold wave type compositions containing 2-iminothiolane.

BACKGROUND OF THE INVENTION

The cold wave type hair waving composition most widely used today in "home kits" is the ammonium thioglycolate type. The alkaline solution of ammonium thioglycolate is applied to the hair for a short time, rinsed, and the treated hair subsequently fixed (oxidized, neutralized) with one of the commercially available products for this purpose, such as a solution of sodium or potassium bromate.

Ammonium thioglycolate is not a completely satisfactory waving compound in that it has an odor which is not agreeable to many users; is a slight eye irritant; and causes damage to the bulk properties of the hair and also causes chemical damage, as evidenced by porosity measurement using copper uptake.

Thus, there is a need for a hair waving composition which is as effective as, or more effective than, ammonium thioglycolate in wave efficiency and curl retention, and which is odorless and less damaging to the hair.

SUMMARY OF THE INVENTION

The present invention is based on the discovery that aqueous alkaline solutions of 2-iminothiolane, provide wave efficiency and curl retention at least equivalent to ammonium thioglycolate, while having less offensive odor and causing less damage to the hair.

Thus, the invention provides hair waving compositions comprising from about 4 to 8 percent by weight of 2-iminothiolane in aqueous alkaline solution at a pH of about 9.2 to 9.5.

DESCRIPTION OF THE INVENTION

2-Iminothiolane is available as the hydrohalide salt, generally as the hydrochloride. It is made according to procedures described by Addor in U.S. Pat. No. 3,318,910, particularly in Example 1 thereof. The compound has minimal and acceptable toxicity.

Hair waving compositions, in accordance with the invention, are readily prepared by dissolving sufficient of the 2-iminothiolane hydrochloride in water to form a solution containing from about 4 to 8 percent by weight, and adjusting the pH to 9.2 to 9.5 with a water soluble base having a dissociation constant of $5 \times 10^{-3}$ or greater. Suitable bases include aqueous ammonia, which is preferred, or an organic water soluble amine, such as mono-, di-, or triethanolamine, or guanidine.

The wave efficiency of the compositions will depend on the concentration of 2-iminothiolane. A light to medium wave results from concentrations of 4–5 percent, while a permanent wave results from a concentration of 6–8 percent.

The method of application is the same as is used with the conventional ammonium thioglycolate compositions. Thus, the previously rinsed or shampood hair is set in curls and saturated with the solution of 2-iminothiolane. After a short period of time, the hair is rinsed and then treated with a neutralizer solution, rinsed and dried.

A. The waving efficiency of the composition is determined as follows:

1. 0.5 gram of straight, virgin brown hair (at least 8 inches long) is wound between two rows of pegs on a pegboard 5.5 cm × 1.5 cm, containing 14 pegs spaced 0.3 cm apart and 2 cm high. The hair is wound smoothly and evenly, care being taken not to twist the hair. Each end of the hair is secured with a rubber band and a strip of blotting paper is wrapped around the pegboard and secured with a rubber band.

2. The hair and the blotting paper are completely saturated with 4 cc of the waving solution and the pegboard is placed in an 8-ounce jar, covered and suspended in a 25° C. constant temperature bath.

3. After 15 minutes, the jar is removed from the bath and the pegboard from the jar. The blotting paper is removed and the hair is rinsed for 30 seconds in water.

4. The pegboard is then placed in a commercial neutralizer solution for 15 minutes and the hair is then rinsed for one minute in cool water and removed from the pegboard.

5. The hair is placed in a pan containing about 3 inches of water and allowed to relax for 5 minutes.

6. The curl is then laid on a table and measured from the first to the sixth crest of the wave.

7. Percent waving efficiency $= 100 - \frac{100 (B - A)}{C - A}$ where
A = distance between first and sixth peg on pegboard = constant = 2.7 cm.
B = linear measurement of waved hair, in cm.
C = length (cm) of straight hair used to measure six curl crests = constant = 14.8 cm.

Following the precedure of Paragraph A, the following solutions were prepared and evaluated for waving efficiency:

|  | Parts by Weight | |
| --- | --- | --- |
|  | A | B |
| Ammonium thioglycolate (59.3%) | 11.97 | — |
| 2-Iminothiolane hydrochloride | — | 7.1 |
| Ammonium hydroxide | to pH 9.2–9.5 | |
| Deionized water | qs to 100 grams | |

Results obtained are as follows:

|  | Waving Efficiency, % | |
| --- | --- | --- |
| Treatment | at 25° C. | at 37° C. |
| Solution A | 52.34 | 64.47 |
| Solution B | 53.45 | 64.46 |

The data demonstrate that 2-iminothiolane is as efficient as ammonium thioglycolate in permanent waving compositions.

B. Chemical damage to the hair is determined by copper absorption. Hair samples, 500 mg, are soaked in 50 ml of 0.1N tetraamine copper sulfate at 32° C. for 15 minutes, followed by washing with distilled water. The filtrate is then titrated against 0.1N sodium thiosulfate to determine the amount of copper absorbed by the hair.

Using this procedure, virgin brown tresses were treated with solutions A and B above and the extent of chemical damage to the tresses was evaluated with the following results:

| Hair Type | Mg Cu Absorbed per 0.5 gm Hair* | Mg Cu Absorbed* | % Cu Absorbed by the Hair* |
|---|---|---|---|
| Virgin Brown (untreated) | 7.461 | — | — |
| Treated with Solution A | 19.289 | 11.928 | 2.386 |
| Treated with Solution B | 11.218 | 3.757 | 0.751 |

*Average of 3 Tresses

The data clearly indicate that 2-iminothiolane is less damaging to the hair than ammonium thioglycolate.

C. Curl retention was evaluated by saturating virgin hair tresses, wound on ¼" permanent wave rods, with 4 cc of solution under test per tress. The solutions are allowed to stay on the hair for 15 minutes, then rinsed with tepid water and towel blotted. A neutralizer is then applied, allowed to remain for 5 minutes, and then rinsed and the tresses removed from the rods. The tresses are then rolled on to ½" rollers and dried in a salon type drier. The tresses are placed in a constant humidity chamber and measurements for curl retention taken initially and at 30-minute intervals for 2 hours.

Following the above procedure, solutions A and B were evaluated for curl retention with the following results:

| Treatment | Percent Curl Retention* | | | |
|---|---|---|---|---|
| | 30 Min. | 60 Min. | 90 Min. | 120 Min. |
| Water | 28.84 | 27.06** | — | — |
| Solution A | 52.09 | 44.92 | 41.57 | 41.57 |
| Solution B | 54.00 | 50.21 | 48.06 | 48.06 |

*71° F. @ 85% RH; average of 20 tresses
**Evaluation was stopped after 60 minutes due to rapid fall of curls on untreated tresses.

The data indicate that 2-iminothiolane provides improved curl retention in a humid atmosphere.

We claim:

1. A composition for producing a permanent wave in hair consisting essentially of an aqueous solution of 4 to 8 percent by weight of 2-iminothiolane and a water soluble base having a dissociation constant of at least $5 \times 10^{-3}$ in an amount to impart a pH of 9.2 to 9.5 to said composition.

2. A composition in accordance with claim 1 comprising from about 6 to 7.5 percent by weight of 2-iminothiolane.

3. A composition in accordance with claim 1 wherein said base is aqueous ammonia.

4. A composition in accordance with claim 3 wherein said base is monoethanolamine, diethanolamine or triethanolamine.

5. A method for improving the curl retention of hair which comprises applying thereto, in an amount sufficient to saturate the hair, a composition comprising from about 4 to 8 percent by weight of 2-iminothiolane in an aqueous alkaline solution having a pH of from about 9.2 to 9.5, and allowing the composition to remain on the hair for a time sufficient to allow the 2-iminothiolane to enhance the curl retention properties of the hair.

6. A method in accordance with claim 5 wherein the hair is rinsed following treatment with 2-iminothiolane and the hair neutralized with an aqueous solution of an alkali metal bromate or a solution of an alkali metal bromate, an alkali metal borate and boric acid, and dried.

* * * * *